United States Patent [19]

Harrison et al.

[11] 4,042,458
[45] Aug. 16, 1977

[54] PROCESS FOR THE PRODUCTION OF MICRO-ORGANISMS

[75] Inventors: David E. F. Harrison; Harmannus J. Doddema, both of Faversham, England

[73] Assignee: Shell Oil Company, Houston, Tex.

[21] Appl. No.: 665,641

[22] Filed: Mar. 10, 1976

[30] Foreign Application Priority Data

Mar. 14, 1975 United Kingdom .............. 10745/75

[51] Int. Cl.² ............................................. C12B 1/00
[52] U.S. Cl. ................................... 195/28 R; 195/49; 195/96; 195/111
[58] Field of Search ................. 195/28 R, 96, 49, 111, 195/115

[56] References Cited

U.S. PATENT DOCUMENTS 3,930,947  1/1976  Morinaga et al. ..................... 195/96

FOREIGN PATENT DOCUMENTS 2,407,740  2/1974  Germany ............................. 195/111

OTHER PUBLICATIONS

Vary et al., "Cell Yields of Bacteria Grown on Methane" Applied Microbiology Nov. 1967, pp. 1473–1478.

*Primary Examiner*—Alvin E. Tanenholtz
*Assistant Examiner*—R. B. Penland

[57] ABSTRACT

A process for the production of micro-organisms in which a methane-utilizing strain of *Methylococcus* is grown under aerobic conditions in a liquid growth medium comprising methane in the presence of non-methane utilizing micro-organisms.

9 Claims, No Drawings

PROCESS FOR THE PRODUCTION OF MICRO-ORGANISMS

BACKGROUND OF THE INVENTION

This invention relates to a process for the production of micro-organisms. Many micro-organisms are known which can utilise hydrocarbons or certain oxygenated or other derivatives thereof as their carbon and/or energy source. The dried biomass obtainable by the cultivation of such micro-organisms, often referred to as single cell protein (SCP), is rich in protein and can be used as a possible food-stuff or food supplement for man and animals. Of particular interest in this connection are micro-organisms which are capable of utilising gaseous organic compounds containing one or more carbon atoms in their molecules, for example methane.

It is an object of the present invention to provide an improved process for the cultivation of methane-utilising micro-organisms.

SUMMARY OF THE INVENTION

Accordingly the present invention provides a process for the production of micro-organisms comprising culturing, under aerobic conditions in a liquid growth medium comprising assimilable sources of nitrogen and essential mineral salts in the presence of methane gas, a methane-utilising microorganism which is a strain of Methylococcus in the presence of (a) one or more methanol-utilising micro-organisms which is/are capable of metabolising methanol produced by the growing methane-utilising micro-organism, and (b) one or more non-methylotrophic micro-organisms which is/are capable of metabolising organic substances produced by the methane and/or methanol utilising micro-organisms, and recovering the microorganisms from the liquid growth medium.

A methane-utilising micro-organism particularly useful in the process of the present invention is the strain Methylococcus 999 which is a new bacterium strain and has been designated as such by the inventors. This strain has the NCIB Accession No. 11083. Other methane-utilising bacteria may also be present in the culture, for example Methylomonas SM3 (NCIB No. 11084), which has been described in the Netherlands patent application No. 74 16644.

Suitable methanol-utilising micro-organisms for use in the process of the invention include strains of Hyphomicrobium (for example NCIB No. 11040), *Pseudomonas extorquens* and *Pseudomonas methylotropha* (for example NCIB Nos. 10,508 – 10,515 and 10,592 – 10,596) and in particular obligate methanol-utilising micro-organisms such as the strain designated OML (NCIB No. 11112), which has been described in the Netherlands patent application No. 74 16644.

Examples of suitable non-methylotrophic micro-organisms for use in the process of the invention include strains of Pseudomonas (for example NCIB Nos. 11019 and 11022), Acinetobacter (for example NCIB No. 11020), Curtobacterium (for example NCIB No. 11021), *Nocardiaceae, Mycobacteriaceae* and Achromobacteriaceae and in particular Mycobacterium (NCIB No. 11061) and three Pseudomonas strains (NCIB Nos. 11062, 11063, 11065) which have been described in the Netherlands patent application No. 74 16644.

Mixed cultures for use in the process of the invention may be obtained in the following ways:

a. Mixed cultures comprising a methane - utilising micro-organism in association with one or more methanol-utilising micro-organisms and one or more non-methyl-otrophic micro-organisms may be isolated from natural sources. A particularly useful mixed culture for use in the process of the invention (hereinafter designated T4) comprises Methylococcus 999 (NCIB No. 11083), OML (NCIB No. 11112), Mycobacterium (NCIB No. 11061) and three Pseudomonas strains (NCIB Nos. 11062, 11063, 11065).

b. Suitable mixed cultures may also be obtained by combining one or more strains of Methylococcus with one or more strains of methanol-utilising micro-organisms and one or more strains of nonmethylotrophic micro-organisms.

The strain Methylococcus 999 (NCIB No. 11083) is a novel micro-organism which also grows well as a pure culture in a liquid medium and accordingly the invention also provides this novel micro-organism as well as a process for the production of micro-organisms comprising culturing, under aerobic conditions in a liquid growth medium comprising assimilable sources of nitrogen and essential mineral salts in the presence of methane gas, this micro-organism, and recovering the micro-organisms from the liquid growth medium.

This new strain, Methylococcus 999, also grows well on methane in the presence of one or more non-methylotrophic micro-organisms without the addition of methanol-utilising micro-organisms. Accordingly the invention also provides a process for the production of micro-organisms comprising culturing, under aerobic conditions in a liquid growth medium comprising assimilable sources of nitrogen and essential mineral salts in the presence of methane gas, the micro-organism Methylococcus 999 (NCIB No. 11083) in the presence of one or more non-methylotrophic micro-organisms which is/are capable of metabolising substances produced by the micro-organism Methylococcus 999 (NCIB No. 11083). If urea is used as a source of nitrogen the strain Methylococcus 999 is preferably grown in the presence of a urease positive non-methylotrophic micro-organism.

The mixed culture T4, which is particularly preferred in the process of the invention, was isolated from a mud sample taken from a tropical duck farm. Two grammes of the mud sample were put into a 250 ml shake-flask containing 25 ml of 1-NSM medium (as hereinafter described) and gassed twice daily with a gas mixture consisting of 40%v. methane, 50%v. air and 10%v. $CO_2$. The flask was incubated on a rotary shaker of orbital radius 2.5 cm at 200 rpm for one week at 40° C. The culture, in which turibidity had developed, was sub-cultured using 2 ml of inoculum into similar shake-flasks observing aseptic precautions. This was repeated several times and when good growth was obtained the shake-flask culture was used to inoculate a continuous culture under the conditions described in Example 1. After more than 1,000 hours of continuous culture a stable mixed bacterial culture had developed in which the predominant organism was a coccoid methane-utilising bacterium. The characteristics of the mixed culture, designated T4, are described in detail herebelow.

The isolation of a pure culture of the methane-utilising micro-organism from the mixture T4 proved to be impossible using conventional agar plating techniques as only mixed colonies formed on the plates that way.

As it appeared that when using these techniques the growth of the methane-utilising organism was dependent on the presence of heterotrophic (non-methylotrophic) bacteria in the mixture, the following procedure was adapted: 1 ml of the mixed culture T4 (approximately 2 g/l) was mixed with 40 ml of a sterile molten solution (55° C) of one percent Bacto Difco Agar in 2-ASM medium (as hereinafter described), the mixture poured into sterile petri dishes and allowed to set.

A second layer of agar was poured on top of this and a sterile Millipore membrane filter was placed on top of the second layer. Samples of the mixed culture T4 were streaked onto the membrane. Colonies were observed after 4 days incubation at 40° C. These were found to be pure colonies of the coccoid methane-utilising bacterium, Methylococcus 999 (NCIB No. 11083).

This isolated organism would not grow, as a pure culture, on agar plate unless a very heavy inoculum was used or unless the overlay technique described above was employed. However, the bacterium grew well as a pure culture in liquid culture.

The culture T4 comprises the methane-utilising strain Methylococcus 999 (NCIB No. 11083); it also contains one methanol-utiliser (NCIB No. 11112) and four heterotrophs (NCIB Nos. 11061, 11062, 11063, 11065).

The methanol-utiliser and the four heterotrophs have already been described in the Netherlands patent application No. 74 16644.

The methane-utilising organism appeared to be a previously undescribed species of a Methylococcus on basis of the following identification:

| Membrane type | : II stacked membrane, as described by Whittenbury et al., Journal of General Microbiology (1970), 61,205 |
|---|---|
| Cell shape | : cocci |
| Cell diameter | : about 0.9 nm |
| Growth at 37° C | : + |
| Growth at 42° C | : + |
| Growth at 55° C | : + |
| Growth on methanol | : + |
| Enhancement of growth by yeast extract | : − |
| malate | : − |
| acetate | : − |
| succinate | : − |
| Motility | : − |
| Capsule formed | : + |
| Colony colour | : white/brown |
| Water soluble pigment | : − |
| Gram stain | : Gram variable; the Gram stain varied with growth conditions of the cells. Cells harvested from a continuous culture growing on a nitrate medium were Gram positive, but cells obtained from a culture growing on ammonia were Gram negative. |
| Catalase | : + |
| Oxidase | : − |
| Glucose acid | : − |
| OF (Hugh Leifson) | : no reaction |
| Oxidation alkanes | : + |
| Sensitivity to antibiotics | : (+ denotes sensitivity − denotes no sensitivity) |
| Chloramphenicol 10 μg | − |
| Erythromycin 10 μg | : − |
| Sulfafurasol 100 μg | : + |
| Novobiocin 5 μg | : − |
| Oleandomycin 5 μg | : − |
| Pencillin G 1.5 units | : + |
| Streptomycin 10 μg | : + |
| Tetracyclin 10 μg | : + |
| Cephaloridin 5 μg | : − |
| Kenamycin 5 μ: | + + |
| Ampicillin 2 μg | : + |

From these characteristics this organism appears to be a strain of Methylococcus. However, it is distinguished from any previously described strain of Methylococcus in that it will grow at 55° C and does not form colonies on mineral salts agar plates unless the techniques described hereabove are used.

The liquid growth medium used in the process of the invention comprises a nitrogen-containing compound which may be ammonia, urea, an ammonium salt such as a sulphate, chloride or a nitrate, for example an alkali metal nitrate. The compound is suitably present in a concentration from 3–50 g/l.

Other elements which may be present in the medium are phosphorus, sulphur, magnesium and iron. The phosphorus source is preferably one or more phosphates, for example $K_2HPO_4$, $KH_2PO_4$, $Na_2HPO_4$ or $(NH_4)_2HPO_4$, or phosphoric acid, preferably present in a concentration from 3–20 g/l. The sulphur source may be sulphuric acid or a sulphate such as $(NH_4)_2SO_4$ suitably in a concentration from 0.5–5.0 g/l. The two metals are provided as one or other of their salts, for example $MgSO_4.7H_2O$ in a concentration from 0.2–2.0 g/l and $FeCl_3.6H_2O$ in a concentration from 0.01–0.1 g/l.

The medium may also contain trace amounts of other elements in the form of suitable salts, for example calcium, manganese, zinc, cobalt, molybdenum and boron. Examples of suitable media include:
1-NSM of the following composition:

| | | |
|---|---|---|
| $KH_2PO_4$ | 1.6 | grams/liter |
| $Na_2HPO_4$ | 1.16 | " |
| $NaNO_3$ | 1.18 | " |
| $MgSO_4.7H_2O$ | 0.08 | " |
| $FeSO_4.7H_2O$ | 0.014 | " |
| $Ca(NO_3)_2.4H_2O$ | 0.025 | " |
| $CuSO_4.5H_2O$ | $4 \times 10^{-3}$ | " |
| $ZnSO_4.7H_2O$ | $3.4 \times 10^{-4}$ | " |
| $MnSO_4.4H_2O$ | $3 \times 10^{-4}$ | " |
| $Na_2MoO_4.2H_2O$ | $2.4 \times 10^{-4}$ | " |

2-ASM which had the same composition as 1-NSM except that it contained 1.18 g/l $(NH_4)_2SO_4$ instead of $NaNO_3$.

3-USM which had the same composition as 1-NSM except that it contained 2.0 g/l urea instead of $NaNO_3$.

5-C of the following composition:-

| | | |
|---|---|---|
| $KH_2PO_4$ | 1.6 | grams/liter |
| $Na_2HPO_4$ | 1.16 | " |
| $NaNO_3$ | 3.18 | " |
| $MgSO_4 . 7H_2O$ | 0.107 | " |
| $FeSO_4 . 7H_2O$ | 0.009 | " |
| $Ca(NO_3)_2 . 4H_2O$ | 0.06 | " |
| $CuSO_4 . 5H_2O$ | $3 \times 10^{-4}$ | " |
| $ZnSO_4 . 7H_2O$ | $3.6 \times 10^{-4}$ | " |
| $MnSO_4 . H_2O$ | $5 \times 10^{-4}$ | " |
| $Na_2MoO_4 . 2H_2O$ | $3.1 \times 10^{-4}$ | " |
| $CoCl_2 . 6H_2O$ | $1.5 \times 10^{-4}$ | " |

The process of the invention may be carried out batchwise, semi-continuously but preferably in continuous flow culture. To obtain growth the micro-organisms are inoculated into the liquid growth medium which is contacted with a gas mixture containing methane and oxygen. Methane may be supplied in the form of natural gas. For continuous flow culture the micro-organisms may be grown in any suitable adapted fermentation vessel, for example a stirred baffled fermenter or sparged tower fermenter, which is provided either with internal cooling or an external recycle cooling loop. Fresh medium is pumped continuously into the culture at rates equivalent to 0.02 to 1.00 culture volumes per hour and culture is removed at a rate such that the volume of culture remains constant. A gas mixture containing methane and oxygen and possibly carbon dioxide or other gases is contacted with the medium preferably by bubbling continuously through a sparger at the base of the vessel. The source of oxygen for the culture may be air, oxygen or oxygen enriched air. Spent gas is removed from the head of the vessel. Spent gas may be recycled either through an external loop or internally by means of a gas inducer impeller. The gas flows and recycle should be arranged to give maximum growth of organism and maximum utilisation of methane.

The temperature of the culture is generally maintained between 30° to 60° C and preferably from 38° to 50° C. The pH of the culture is controlled at a pH between 6.0 and 8.0 and preferably between 6.0 and 7.0 by the appropriate addition of an alkali, for example NaOH, KOH, $NH_4OH$, and/or an acid, for example $H_2SO_4$ or $H_3PO_4$.

The micro-organism cells may be harvested from the growth medium by any of the standard techniques commonly used, for example flocculation, sedimentation, and/or precipitation, followed by centrifugation and/or filtration. The biomass is then dried e.g. by freeze or spray drying and may be used in this form as a protein food stuff or food supplement for man or animals. The invention is illustrated further in the following examples.

EXAMPLE I

Continuous cultures of both the mixed culture T4 and a pure culture of Methylococcus 999 were grown under aseptic conditions in stirred fermenters of 2.5 litres working volume (Biotec Fermenter, LKB Co. Ltd.,). Methane/air mixtures (ratio 2/1 v/v) were bubbled through the liquid in the fermenters at a rate of 900–1200 ml/min. The temperature of the culture was controlled at 42° C and the pH at 6.8 by the automatic addition of a mixture of 0.5N NaOH and 0.5N KOH. The culture was stirred at a rate of 1200 rpm. Fresh medium was supplied continuously to the culture by means of a peristaltic pump and culture was pumped out at the same rate to maintain a constant volume in the vessel. The medium composition was as follows:

| Component | Concentration (mM) |
|---|---|
| $(NH_4)_2SO_4$ | 11.0 |
| $H_3PO_4$ | 10.0 |
| $MgSO_4$ | 0.4 |
| $CaCl_2$ | 0.1 |
| $FeSO_4$ | $33 \times 10^{-3}$ |
| $ZnSO_4$ | $1.0 \times 10^{-3}$ |
| $MnSO_4$ | $1.0 \times 10^{-3}$ |
| $H_3BO_3$ | $1.0 \times 10^{-3}$ |
| $CuSO_4$ | $0.5 \times 10^{-3}$ |
| $Na_2MoO_4$ | $0.2 \times 10^{-3}$ |
| $CoCl_2$ | $0.2 \times 10^{-3}$ |
| KI | $0.5 \times 10^{-3}$ |
| $H_2SO_4$ | $1.0 \times 10^{-3}$ |

The fermenters were filled with 2 liters of medium, stirred, aerated and supplied with methane and air as described above. Each fermenter was inoculated with 100 ml of fully grown shake flask culture, one with the mixture T4 the other with the pure culture Methylococcus 999. Medium was fed into the fermenters at a range of dilution rates starting from $0.10h^{-1}$, and increasing in steps of approximately $0.02 - 0.03h^{-1}$ until the culture began to wash out of the vessel. Steady-states were maintained at each dilution rate for at least 48 hours. The results are summarised in Table 1.

Table 1

| Culture | Maximum Dilution Rate Achieved $(h^{-1})$ | Dry Weight Conc. $(g\, l^{-1})$ | Yield Coefficient (g dry weight/ $gCH_4$ used) |
|---|---|---|---|
| T4 | 0.34 | 2.42 | 0.71 |
| Methylococcus 999 | 0.31 | 2.14 | 0.66 |

EXAMPLE 2

Batch cultures of the organism Methylococcus 999 only and of this organism in admixture with a urease positive bacilllus, incapable of growing on methane but capable of growth on substances produced by organism Methylococcus 999, were grown at 42° C in a simple salts medium contained in sterile glass vessels of 500 ml capacity through which a continuous supply of a methane, air and $CO_2$ at 25, 100 and 10 ml per minute respectively were bubbled via a sintersol glass filter.

The flasks were inoculated with 1.5 ml of fresh inoculum. The medium in the vessels was 300 ml of 3-USM. Growth was assessed by measuring optical density (OD) at 625 nm. The results are given in Table 2.

The urease positive bacillus was characterized as follows: Gram stain +, rod shaped, non-motile, growth in air +, catalase +, oxidase −, glucose acid (gas) +, OF (Hugh & Leifson) +, urease +, no denitrification.

Table 2

Growth of *Methylococcus* 999 and mixed culture (OD at 625 nm)

| | (mean values of triplicate cultures) | | | |
|---|---|---|---|---|
| Culture/T in hrs | 0 | 24 | 96 | 120 |
| *Methylococcus* 999 only | 0.005 | 0.005 | 0.029 | 0.054 |
| *Methylococcus* 999 mixed with urease positive bacillus | 0.005 | 0.229 | 0.490 | 0.550 |

These results show that the organism Methylococcus 999 grew well on urea only if a urease positive organism was also present.

EXAMPLE 3

The mixed culture T4 was grown with various nitrogen sources under various conditions.

The cultures were grown in 2.5 l stirred vessels as described in Example 1. Although strict ascepsis was not observed in these experiments the microbiological characteristics of the culture did not change.

The culture conditions were: temperature 42° C; pH: 7.0; dilution rate $0.18h^{-1}$; stirring speed: 1000 rpm; total gas flow rate: 600 ml/min. Yield coefficients were calculated from the analysis of the gas stream into and out of the fermenter by means of gas chromatography, and from careful measurement of the gas flow-rates using a bubble flow-meter. The organism dry weight concentration, which has between 4 and 5 g $l^{-1}$, was estimated by measuring the difference in carbon concentration between a culture sample and the culture supernatent after centrifuging a sample at 6000 g for 15 min. The carbon content of oven dried cells was found to be constant at 48%.

The media employed contained (g $l^{-1}$) $KH_2PO_4$: 1.60; $Na_2HPO_4$: 1.16; $MySO_4.7H_2O$: 0.080; $FeSO_4.7H_2O$: 0.014; $Ca(NO_3)_2 4H_2O$: 0.025; $2.4 \times 10^{-3}$; $ZnSO_4.7H_2O$: $3.4 \times 10^{-4}$; $MnSO_4.4H_2O$: $3.0 \times 10^{-6}$; $NaMoO_4.2H_2O$: $2.4 \times 10^{-4}$; $CoCl^2.6H_2O$: $1.5 \times 10^{-4}$, concentrated sulphuric acid (36 N) was added at 0.33 ml. per litre. As nitrogen source $NaNO_3$ (3.18 g $l^{-1}$), $(NH_4)_2SO_4$ (2.46 g $l^{-1}$) or urea (1.122 g $l^{-1}$) was added.

The results are shown in Table 3.

Table 3

| Effect of nitrogen source and limiting factor on continuous cultures of mixture T4 | | | | | |
|---|---|---|---|---|---|
| Nitrogen Source: | NaNO₃ | | (NH₄)₂SO₄ | | Urea |
| Air/methane ratio in gas supply: | 3:1 | 6:1 | 3:1 | 6:1 | 3:1 |
| growth-limiting factor | O₂ | CH₄ | O₂ | CH₄ | O₂ |
| Yield coefficient (g cells/g CH₄) | 0.65 ±0.03 | 0.63 ±0.03 | 0.69 ±0.04 | 0.83 ±0.02 | 0.76 ±0.05 |

EXAMPLE 4

The culture was grown in 7 litre stirred fermenters (Chemap Co. Ltd., Zurich, Switzerland). The temperature was maintained at 42° C and the pH at 7.4 by the automatic addition of a 5N solution of a KOH/NaOH mixture (1:1) or 5 N $H_2SO_4$ as required. A mixture of oxygen, and methane was gassed through the fermenter at 2 l/min. The fermenter was stirred at 1500 rpm. The volume in the fermenter vessel was maintained at 4.4 liters by means of an overflow weir out through which culture was continuously pumped. Medium was supplied to the culture in two streams, i.e. 1) solution of $NH_4SO_4$ (150 mM), $H_3PO_4$ (45 mM), $MgSO_4$ (4.5 mM), $CaCl_2$ (1.5 mM), $FeSO_4$ (0.6 mM) and 26.4 ml of a solution containing (g liter) $ZnSO_4.7H_2O$: 0.18; $CuSO_4.5H_2O$: 0.16; $MnSO_4.4H_2O$: 0.15; $CoCl_3.6H_2O$: 0.18; $H_3BO_3$: 0.1; $NaMoO_4.2H_2O$: 0.3; and 2) de-ionised water. These were pumped continuously into the culture such that the total flow rate was always equivalent to a culture dilution rate of $0.09h^{-1}$. The relative flow-rates of the salts and the water streams were varied. As the gas supply was more than sufficient, the culture concentration was limited by the concentration of nitrogen source in the total feed of medium. Thus increasing the rate of feed of the salt solution relative to the water stream, increased the organism concentration in the culture.

Starting at an organism dry weight concentration of 4.2 g $l^{-1}$, the flow-rate of the salt solution was increased until an organism dry weight concentration of 23 g $l^{-1}$ was achieved and a steady-state maintained at this level.

EXAMPLE 5

Culture of the organism Methylococcus 999 and the mixture T4 were grown in continuous culture as described in Example 1 on medium 5-C, at a dilution rate of $0.08h^{-1}$. The cells were harvested from the culture pumped out of the fermenter vessel, centrifuged and freeze-dried. The protein content (calculated as N × 6.25) of both was 69%. The aminoacid analysis of cells from the two cultures is shown in Table 4.

Table 4

| Amino-acid content of cells from T4 and strain 999 | | |
|---|---|---|
| | % crude protein (g/16gN) | |
| Amino-acid | T4 | 999 |
| Aspartic Acid | 8.55 | 8.29 |
| Threonine | 4.42 | 4.34 |
| Serine | 3.49 | 3.40 |
| Glutamic Acid | 9.39 | 9.27 |
| Proline | 7.39 | 6.53 |
| Glycine | 5.41 | 4.68 |
| Alanine | 7.66 | 6.32 |
| Valine | 6.31 | 5.99 |
| Cystine | N/D | 0.57 |
| Methionine | 2.32 | 2.59 |
| Isoleucine | 3.83 | 4.21 |
| Leucine | 7.28 | 7.30 |
| Tyrosine | 2.17 | 3.97 |
| Phenylalanine | 4.59 | 4.65 |
| Ornithine | 0.05 | 0.18 |
| Lysine | 5.49 | 5.24 |
| Arginine | 5.63 | 5.04 |
| Histidine | 2.02 | 2.06 |

We claim:

1. A process for the production of micro-organisms comprising culturing, under aerobic conditions in a liquid growth medium comprising assimilable sources of nitrogen and essential mineral salts in the presence of methane gas, a methane-utilising micro-organism which is a strain of Methylococcus 999 having the NCIB Accession No. 11083 in the presence of (a) methanol-utilising micro-organisms which are capable of metabolising methanol produced by the growing methane-utilising micro-organism, and (b) non-methylotrophic micro-organisms which are capable of metabolising organic substances produced by the methane- and/or methanol-utilising micro-organisms, and recovering the micro-organisms from the liquid growth medium.

2. A process according to claim 1, wherein the methanol-utilising micro-organism is a strain of *Pseudomonas extorquens* or *Pseudomonas methylotropha* having the NCIB Accession Nos. 10,508, 10,515 and 10,592 through 10,596 or the micro-organism strain OML having the NCIB Accession No. 11.112.

3. A process according to claim 1, wherein the methane-utilising micro-organisms, the methanol-utilising micro-organisms and the non-methylotrophic micro-organisms are employed in a mixed culture comprising the organism Methylococcus 999 having the NCIB Accession No. 11083, the strain OML having the NCIB Accession No. 11.112, the species of the genus Mycobacterium having the NCIB Accession No. 11061 and the species of the genus Pseudomonas having the NCIB Accession Nos. 11062, 11063 and 11065.

4. A process according to claim 1, wherein the methaneutilising micro-organism Methylomonas SM3 having the NCIB Accession No. 11084 is also present in the liquid growth medium.

5. A process according to claim 1, wherein the non-methylotrophic micro-organisms are species of the genus Pseudomonas having the NCIB Accession No. 11062, 11063 and/or 11065 and/or a species of the genus Mycobacterium having the NCIB Accession No. 11061.

6. A process according to claim 1, wherein the temperature of the culture is maintained in the range 30° to 60° C.

7. A process according to claim 1, wherein the pH of the culture is controlled in the range 6.0 – 8.0.

8. A process for the production of micro-organisms comprising culturing, under aerobic conditions in a liquid growth medium comprising assimilable sources of nitrogen and essential mineral salts in the presence of methane gas, the micro-organism Methylococcus 999 having the NCIB Accession No. 11083, and recovering the micro-organisms from the liquid growth medium.

9. A process according to claim 8, wherein the micro-organism Methylococcus 999 having the NCIB Accession No. 11083 is growm in the presence of one or more non-methylotrophic micro-organisms which are capable of metabolising substances produced by the micro-organism Methylococcus 999 having the NCIB Accession No. 11083.

* * * * *